United States Patent
Di Miro et al.

(10) Patent No.: US 8,640,526 B2
(45) Date of Patent: Feb. 4, 2014

(54) METHOD AND DEVICE FOR OPERATING A PARTICLE SENSOR

(75) Inventors: Ariel Di Miro, Stuttgart (DE); Enno Baars, Leonberg (DE); Johannes Grabis, Renningen (DE); Alexander Hetznecker, Karlsruhe (DE); Mathias Klenk, Tuebingen (DE); Bernhard Kamp, Ludwigsburg (DE); Bastian Roetzler, Markgroeningen (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 399 days.

(21) Appl. No.: 13/171,535

(22) Filed: Jun. 29, 2011

(65) Prior Publication Data

US 2011/0314899 A1  Dec. 29, 2011

(30) Foreign Application Priority Data

Jun. 29, 2010 (DE) .......................... 10 2010 030 634

(51) Int. Cl.
  *G01N 37/00* (2006.01)
  *G01N 31/00* (2006.01)
  *G01M 15/00* (2006.01)
  *G01R 27/08* (2006.01)

(52) U.S. Cl.
  USPC ......... 73/28.01; 73/1.06; 73/23.3; 73/114.71; 324/693; 702/183

(58) Field of Classification Search
  USPC .......... 73/1.03, 23.33, 28.01, 114.71–114.73; 96/18, 19, 26; 324/693, 702, 703; 701/30.9, 31.1, 114; 702/116, 182, 183
  See application file for complete search history.

(56) References Cited

U.S. PATENT DOCUMENTS

| 7,543,477 | B2 | 6/2009 | Berger et al. |
| 2009/0051376 | A1 | 2/2009 | Schnell et al. |
| 2010/0312488 | A1* | 12/2010 | Diehl et al. ..................... 702/23 |
| 2011/0107815 | A1* | 5/2011 | Nelson et al. ................ 73/23.33 |
| 2011/0156727 | A1* | 6/2011 | Achhammer et al. ........ 324/691 |

FOREIGN PATENT DOCUMENTS

| DE | 10149333 A1 | 5/2003 |
| DE | 102007021910 | 11/2008 |
| WO | 03/006976 A2 | 1/2003 |

* cited by examiner

*Primary Examiner* — Hezron E Williams
*Assistant Examiner* — Nathaniel Kolb
(74) *Attorney, Agent, or Firm* — Michael Best & Friedrich LLP

(57) ABSTRACT

A method for operating a particle sensor (10). The particle sensor (10) has at least two inter-digital electrodes (12, 13) which engage one in the other and to which a sensor voltage $U_{(IDE)}$ (21) is applied in order to determine loading of the particle sensor (10) with soot particles (16). A sensor current $I_{(IDE)}$ (31) across the electrodes (12, 13) is measured and evaluated. In order to remove the loading with soot, a heating element (14) heats the particle sensor (10) in a regeneration phase. The method characterized in that the sensor current $I_{(IDE)}$ (31) is determined, and a shunt diagnosis of the particle sensor (10) is carried out in accordance with the measured sensor current $I_{(IDE)}$ (31).

19 Claims, 2 Drawing Sheets

METHOD AND DEVICE FOR OPERATING A PARTICLE SENSOR

BACKGROUND OF THE INVENTION

The invention relates to a method for operating a particle sensor, wherein the particle sensor has, on its surface, at least two inter-digital electrodes which engage one in the other and to which a sensor voltage $U_{(IDE)}$ is at least temporarily applied in order to determine loading of the particle sensor with soot particles, and a sensor current $I_{(IDE)}$ across the electrodes is measured and evaluated, wherein, in order to remove the loading with soot, a heating element can be additionally provided, with which heating element the particle sensor is heated in a regeneration phase.

The invention also relates to a corresponding device for carrying out the method according to the invention, wherein the particle sensor is connected to an engine controller or a sensor control unit, and the engine controller or the sensor control unit has devices for diagnosing the loading of the particle sensor with soot.

Particle sensors are used today, for example, for monitoring the emission of soot by internal combustion engines and for on-board diagnostics (OBD), for example for functional monitoring of particle filters. In this context, collective, resistive particle sensors are known which evaluate a change in the electrical properties of an inter-digital electrode structure on the basis of accumulations of particles. Two or more electrodes may be provided which preferably engage one in the other in a comb-like fashion. The electrodes are short-circuited by an increasing number of particles which accumulate on the particle sensor, and this can result in an electrical resistance which decreases as the accumulation of particles increases, a decreasing impedance or in a change in a characteristic variable, such as a voltage and/or a current, which is associated with the resistance or the impedance. For the purposes of evaluation, a threshold value, for example of a measuring current between the electrodes, is generally defined, and the time until the threshold value is reached is used as a measure of the accumulated quantity of particles. Alternatively, a rate of change of the signals can also be evaluated during the accumulation of particles. If the particle sensor is fully loaded, the accumulated particles are burnt off in a regeneration phase using a heating element which is integrated in the particle sensor.

Such a resistive particle sensor is described in DE 101 33 384 A1. The particle sensor is constructed from two comb-like electrodes which engage one in the other and which are at least partially covered by a capturing sleeve. If particles from a gas stream become deposited on the particle sensor, this leads to a change in the impedance of the particle sensor which can be evaluated and from which the quantity of accumulated particles, and therefore the quantity of particles carried along in the exhaust gas, can be inferred.

DE 101 49 333 A1 describes a sensor device for measuring the moisture of gases, with a resistance measuring structure which is arranged on a substrate, wherein the measuring structure interacts with a layer of soot, and a temperature measuring device is provided. This sensor device can also be used to determine the concentration of soot in the exhaust gas of an internal combustion engine.

DE 10 2004 028 997 A1 discloses a method for controlling the accumulation of particles on a sensor element which has a first electrode and a further electrode and to which a first voltage $U_1$ and a second voltage $U_2$ can be applied at voltage terminals. There is provision here that the sensor element can be operated with a raised voltage $U_1$ during a first time period $t_1$, and, after a triggering threshold AP of the sensor element has been exceeded, said sensor element can be operated with a lower voltage $U_2$, which is lower than the raised voltage $U_1$. The method permits the time after regeneration of the sensor element in which no measuring signal is available until the time at which a signal which can be evaluated is obtained as a result of accumulation of a sufficient quantity of particles to be shortened by virtue of the fact that the sensor element is operated with a raised operating voltage during this phase. The raised operating voltage brings about an increased rate of accumulation of particles on the sensor element. If a sufficiently large quantity of particles has accumulated on the sensor element, so that a measuring signal which can be used is present, the sensor element is operated with a lower voltage with a correspondingly lower rate of accumulation of particles, with the result that the measuring period up to the next necessary regeneration of the sensor element is lengthened. The method accordingly provides two successive operating phases, a first phase with a raised operating voltage during which there is still no adequate measuring signal present, and a second phase with a reduced voltage during which the actual measurement of the particle concentration takes place. In this context, the resistance or the impedance of the sensor element is determined during both phases by means of a corresponding current measurement, on the one hand for detecting the triggering threshold and on the other hand for determining the rate of accumulation of particles. In both phases, a defined accumulation of particles is necessary. The selected voltages in both phases accordingly constitute a compromise between optimized accumulation of particles and precise measurement of resistance or impedance.

DE 103 19 664 A1 discloses a sensor for detecting particles in a gas stream, in particular particles of soot in an exhaust gas stream, having at least two measuring electrodes which are arranged on a substrate made of an electrically insulating material. In this context there is provision that the measuring electrodes are coated by a protective layer. The protective layer protects the electrodes against corrosion under extreme environmental conditions. In this context, the protective layer can be embodied as an electrical conductor or as an electrical insulator. A conductive protective layer permits the particle concentration to be determined through resistance direct current measurement, in which case a parallel connection between the electrodes is produced by means of the protective layer and the accumulated particles. In the case of an insulating protective layer, it is necessary to measure the impedance using an alternating voltage.

In order to regenerate the particle sensor after particles have accumulated, the sensor element is burnt clean using an integrated heating element. This must be carried out at certain time intervals in order to avoid falsification in the determination of the particle concentration.

The start of regeneration is usually triggered by the current across the sensor element, the so-called IDE current or sensor current $I_{(IDE)}$, exceeding a defined threshold value current. The concentration of soot in the exhaust gas can be inferred from the time until the threshold value current is reached.

In order to be able to obtain a high level of sensor accuracy, it is decisive to be able to determine as accurately as possible the time when the defined evaluation threshold is reached. Since the threshold currents are typically in the region of several µA, the signal can easily be falsified by shunts, for example owing to moisture condensing on the sensor. The separation of these shunt currents from the searched-for IDE current has hitherto presented a challenge for the development of sensors.

SUMMARY OF THE INVENTION

For the sake of improved self-diagnosis and increased sensor accuracy, the object of the invention is to make available a corresponding method which permits an improved method of functioning of the system while avoiding cross sensitivities owing to these shunts.

The object of the invention is also to make available a corresponding device for carrying out the method.

The object relating to the device is achieved in that the engine controller or the sensor control unit has devices for determining a shunt current $I_{(N)}$, and on the basis of the shunt current $I_{(N)}$ it is possible to correct a triggering threshold for regeneration of the particle sensor or to perform self-diagnosis of the particle sensor. In this context it is possible provide for the functionality of the method variants to be implemented as software in the engine controller or in the sensor control unit.

The method provides that the sensor current $I_{(IDE)}$ is determined when a minimum value of the sensor current $I_{(IDE)}$ is reached or after a certain waiting time after a certain sensor element temperature threshold has been undershot or directly when the sensor element temperature threshold is undershot, and a shunt diagnosis of the particle sensor is carried out in accordance with the measured sensor current $I_{(IDE)}$.

In order to avoid shunts between the measuring electrodes over the service life of the particle sensor, which shunts reduce the sensor accuracy, it is usually necessary to make considerable expenditure in terms of the use of corresponding materials and techniques in the fabrication process. With the method according to the invention and the device for carrying out the method it is possible to tolerate lower shunt resistance and therefore to reduce the expenditure on the manufacture of the particle sensors, which is advantageous in terms of manufacturing costs. In this context it is possible to achieve an equally high level of sensor accuracy with a simpler and therefore more favorable sensor element since cross-sensitivity owing to these shunts during the diagnosis is reduced and can be correspondingly corrected. The time for the shunt diagnosis, as is provided by the method according to the invention, makes it possible to sense the influence of these shunts very precisely in quantitative terms, since said influence always takes place within defined operating phases of the particle sensor, in which case the sensing time can be associated with a temperature threshold being undershot if the temperature of the sensor element is known as a measured value. During the sensing of the sensor current $I_{(IDE)}$ when a minimum value of the sensor current $I_{(IDE)}$ is reached, use is made of the face that, for example after regeneration, the current briefly drops to a minimum value before the first soot shunts are already closed again, with the result that the minimum value of the current across the measuring electrodes or the current which is measured at a fixed time can be evaluated as a measure of the shunt.

In one preferred method variant there is provision that, on the basis of the shunt diagnosis, a shunt current $I_{(N)}$ is determined for a triggering threshold for the sensor current $I_{(IDE)}$ at which a regeneration of the particle sensor is started, and a corrected triggering threshold is determined with said shunt current $I_{(N)}$ as an offset correction, or the regeneration of the particle sensor is started with a time delay when the triggering threshold is reached, as a function of the shunt current $I_{(N)}$. The shunt current $I_{(N)}$ can also be stored here for subsequent triggering of a particle sensor regeneration for the purpose of correction. As a result, all the influences of slowly changing shunts, i.e. those which are longer than a sensor triggering time, on the accuracy can be completely eliminated. Changes of greater than 10% of the typical sensor triggering time are also sensed for the correction of the measured triggering time.

A further preferred method variant provides that the shunt diagnosis or the offset correction of the triggering threshold is carried out after a sensor regeneration since after a sensor regeneration the senor element is cleared of soot and it can be expected that the sensed current flow is not due to soot but rather to parasitic currents.

One method variant provides that the shunt diagnosis and/or the offset correction of the triggering threshold be carried out after a certain time after the switching off of the heating element, wherein the time is predefined by means of a timer, and wherein the time is obtained from the time constant for the cooling behavior of the particle sensor and can be set as constant in this simple method variant.

It is to be noted that a combination of the abovementioned method variants can also be applied. It is therefore advantageous, for example, if, after a predefined temperature threshold has been undershot, in addition waiting is performed under timer control before the shunt current $I_{(N)}$ is sensed. In this context it may, in particular, be appropriate, after the temperature threshold has been undershot, firstly to switch on the supply voltage of the IDE, i.e. the sensor voltage $U_{(IDE)}$, and then to wait, under timer control, for a waiting time after which the shunt current $I_{(N)}$ is sensed.

One preferred use of the shunt current $I_{(N)}$ which is determined during the shunt diagnosis provides that said shunt current $I_{(N)}$ is subtracted from the measured sensor current $I_{(IDE)}$ during the normal operation. With this offset correction it is possible to eliminate parasitic effects in relation to the sensing time, during the normal operation of the particle sensor, subsequently or in advance, with the result that only the sensor current $I_{(IDE)}$ which is due alone to loading with soot can be evaluated during the determination of the loading with soot. As a result, the cross-sensitivity of the particle sensor can be reduced.

If, as is advantageous for self-diagnosis of the particle sensor, the shunt current $I_{(N)}$ which is determined during the shunt diagnosis is compared with a fixed, predefined threshold value or with a temperature-dependent threshold value for a maximum shunt current $I_{(N)}$, it is possible to detect a shunt fault when the fixed threshold value or the temperature-dependent threshold value is exceeded. This threshold value can be stored here as a characteristic curve or characteristic diagram within the engine controller or the sensor control unit.

One particularly preferred method variant provides that the shunt current $I_{(N)}$ which is determined during the shunt diagnosis is determined multiply and averaged or is determined by means of a low-pass filter. As a result, measuring errors which can occur due to brief signal disruption owing to, for example, induced voltages, can be eliminated. As a result, the shunt current $I_{(N)}$ which is determined can be debounced. Furthermore, it is possible to provide that, in order to avoid false alarms, any defects owing to excessively high shunt currents $I_{(N)}$ during the self-diagnosis of the particle sensor can be signaled to a superordinate control unit only after the defect has occurred repeatedly.

In the methods described above and the variants thereof it is possible to provide that a resistance or a conductance value between the electrodes of the sensor structure is evaluated as an equivalent variable for the sensor current $I_{(IDE)}$, wherein sensing of a maximum value for the shunt diagnosis is used in the evaluation of the resistance.

One preferred application of the method variants, as has been described previously, provides for the self-diagnosis of the particle sensor within the scope of an on-board diagnosis in a diesel internal combustion engine. This application crucially involves, in particular, precise and reproducible diagnosis of the loading of a diesel particle filter (DPF) arranged in the exhaust chain of the diesel internal combustion engine with particles. The time of regeneration of the diesel particle filter can be determined accurately by eliminating the parasitic shunts.

BRIEF DESCRIPTION OF THE DRAWINGS

The invention will be explained in more detail below with reference to an exemplary embodiment which is illustrated in the figures. In the drawings.

DETAILED DESCRIPTION

Figure 1:
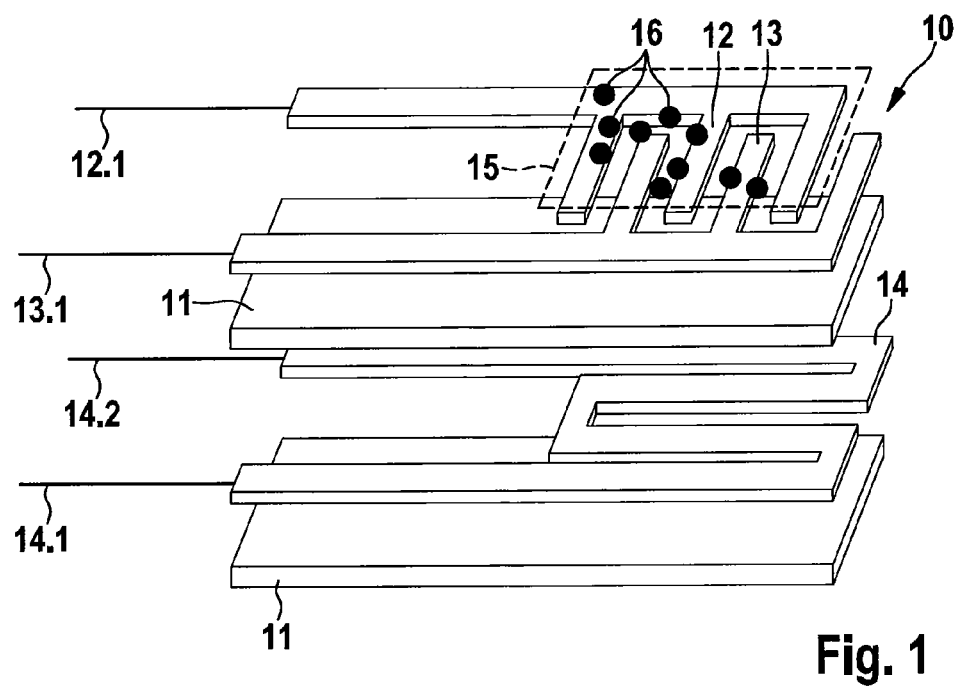
FIG. 1 is a schematic view of a particle sensor in an exploded illustration.

FIG. 1 is a schematic illustration of a particle sensor 10 corresponding to the prior art in an exploded illustration.

A first electrode 12 and a second electrode 13 are mounted on insulator carrier layers 11, for example made of aluminum oxide. The electrodes 12, 13 are embodied in the form of two inter-digital comb electrodes which are engaged one in the other. A first connection 12.1 and a second connection 13.1, via which the electrodes 12, 13 can be connected to a sensor control unit (not illustrated) in order to supply voltage and to carry out the measurement, are provided at the ends of the electrodes 12, 13.

In addition, in the example shown a heating element 14, which is connected to the sensor control unit via the connections 14.1, 14.2, is integrated between the insulating carrier layers 11.

If such a particle sensor 10 is operated in a particle-conducting gas stream, for example in an exhaust gas duct of a diesel engine, the particles from the gas stream accumulate on the particle sensor 10. In the case of the diesel engine, the particles are soot particles 16 with a corresponding electrical conductivity. Here, the rate of accumulation of the soot particle 16 on the particle sensor 10 depends both on the particle concentration in the exhaust gas and also, inter alia, on the voltage which is applied to the electrodes 12, 13. The voltage which is applied generates an electrical field which exerts a corresponding attraction force on electrically charged soot particle 16 and on soot particles 16 with a dipole charge. The rate of accumulation of the soot particles can therefore be influenced by suitable selection of the voltage which is applied to the electrodes 12, 13.

In the exemplary embodiment, the electrodes 12, 13 and the uppermost insulation carrier layer 11 on which the electrodes 12, 13 are located are coated with a protective layer 15. This optional protective layer 15 protects the electrodes 12, 13 against corrosion at the usually prevailing high operating temperatures of the particle sensor 10. In the present exemplary embodiment, said protective layer 15 is manufactured from a material with a low conductivity, but it can also be fabricated from an insulator.

The soot particles 16 from the gas stream have accumulated in the form of a layer on the protective layer 15. As a result of the protective layer 15 which is a poor conductor, the soot particles 16 form conductive soot paths between the electrodes 12, 13, with the result that, depending on the quantity of accumulated soot particles 16, a change in resistance occurs between the electrodes, 12, 13. This change in resistance can be measured, for example, by applying a constant voltage, a sensor voltage $U_{(IDE)}$, to the connections 12.1, 13.1 of the electrodes 12, 13, and by determining the change in the sensor current $I_{(IDE)}$ 31 (cf. in this respect FIG. 3) by means of the accumulated soot particles 16.

If the protective layer 15 is of insulating design, the accumulated soot particles 16 bring about a change in the impedance of the particle sensor 10, and this can be evaluated by means of a corresponding measurement, preferably with an alternating voltage.

Figure 2:
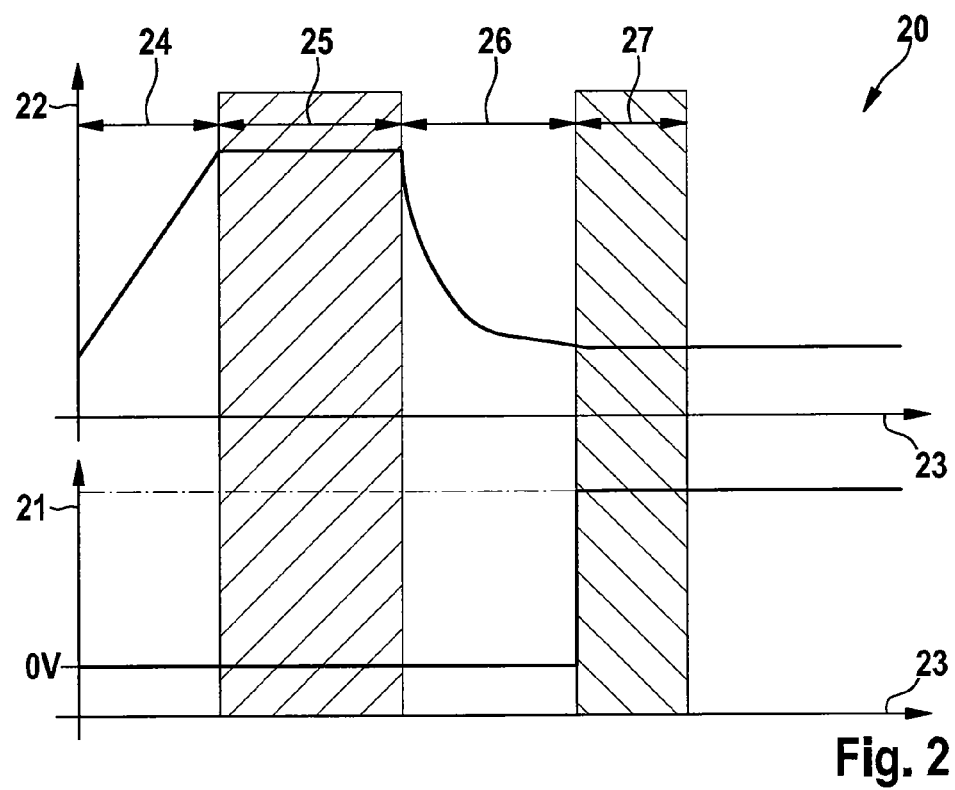
FIG. 2 is a schematic illustration of the time profile of the temperature and of the sensor voltage $U_{(IDE)}$ during a regeneration phase.

FIG. 2 describes the typical profile of a temperature 22 of a sensor element of a particle sensor 10 and the time profile of the sensor voltage $U_{(IDE)}$ 21 during a regeneration phase of the particle sensor 10, in a schematic diagram 20 as a function of the time 23.

When the sensor voltage $U_{(IDE)}$ 21 is switched off, the temperature 22 of the sensor element is firstly raised in a ramp section 24 until a burning clean temperature is reached. This is followed by a burning clean section 25 in which this burning clean temperature is maintained for a certain time, and the soot is burnt off. After this burning clean section 25, the time period of which may be of different lengths depending on the sensor type or particle sensor used, there is an adjoining cooling section 26 in which the temperature 22 drops from the burning clean temperature back to the normal operating temperature of the particle sensor 10, and the regeneration process is terminated and the sensor element is cleaned of soot. A method variant according to the invention provides that, after a temperature threshold for the temperature 22 of the sensor element has been undershot in a testing section 27, the sensor voltage $U_{(IDE)}$ 21 is switched on as a quasi regeneration success test and a shunt diagnosis is carried out.

Figure 3:
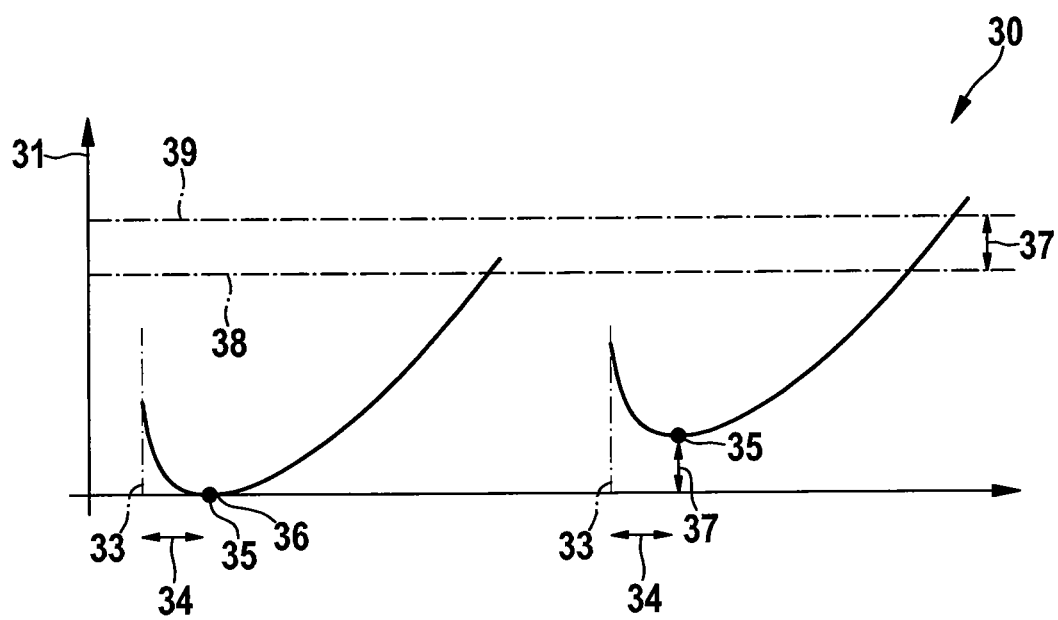
FIG. 3 is a schematic illustration of the means of determining a shunt current $I_{(N)}$ of the particle sensor and a correction of a triggering threshold, derived therefrom, for the regeneration process.

FIG. 3 describes, by way of example in a further diagram 30, the determination of a shunt current $I_{(N)}$ of the particle sensor 10 and of a correction, derived therefrom, of a triggering threshold 38 for the triggering of a regeneration process.

The sensor current $I_{(IDE)}$ 31 is illustrated as a function of the time 32. In the left-hand part of the diagram 30, the sensor current $I_{(IDE)}$ 31 firstly drops, after a triggering time 33, to a minimum value of 35 within a waiting time 34. In the case of an ideal sensor element, which does not have any parasitic shunts, a shunt current $I_{(N1)}$ 36 is near to zero. As a result of loading with soot in the normal operation of the particle sensor 10, the sensor current $I_{(IDE)}$ 31 increases until the triggering threshold 38 for the triggering of the regeneration process is exceeded, and the sensor element has to be correspondingly heated again, as described in FIG. 2. Since in this case a sensor current $I_{(IDE)}$ 31 which is not adversely affected by parasitic shunts is detected, correction of the triggering threshold 38 can be omitted.

The right-hand part of the diagram 30 illustrates the situation which occurs if parasitic shunts occur at the sensor element. In this case, a shunt current $I_{(N2)}$ 37 which is unequal to zero is measured at the minimum value 35 for the sensor current $I_{(IDE)}$ 31. In order to eliminate this shunt effect, there is provision in the example shown that the shunt current $I_{(N2)}$ 37 is added to the value of the current of the triggering threshold 38 in order to define a corrected triggering threshold 39. In another method variant, it is also possible to provide that, when the triggering threshold 38 is reached, delayed activation of the sensor regeneration occurs, with the delay being determined according to the value of the previously determined shunt current $I_{(N2)}$ 37. This relationship can be implemented, for example, in the form of a characteristic curve or characteristic diagram in the engine controller or in the sensor control unit.

With the method according to the invention and the device for carrying out the method it is possible to ensure that shunt currents which adversely affect the accuracy of the particle sensor 10 are detected during the evaluation and correspondingly taken into account in the determination of the time for the start of the regeneration of the particle sensor or of the particle filter.

The indicated diagnostic method is stored in an advantageous embodiment as a method sequence by means of software in the engine controller or a special sensor control unit and is a component of the on-board diagnostics (OBD) for monitoring a diesel particle filter (DPF) by means of resistive particle sensors 10 within the emission control system, as is required by legislators.

The invention claimed is:

1. A method for operating a particle sensor (10), wherein the particle sensor (10) has at least two inter-digital electrodes (12, 13) which engage one in the other and to which a sensor voltage $U_{(IDE)}$ (21) is applied in order to determine loading of the particle sensor (10) with soot particles (16), and a sensor current $I_{(IDE)}$ (31) across the electrodes (12, 13) is measured and evaluated, wherein, in order to remove the loading with soot, a heating element (14) heats the particle sensor (10) in a regeneration phase, characterized in that the sensor current $I_{(IDE)}$ (31) is determined, and a shunt diagnosis of the particle sensor (10) is carried out in accordance with the measured sensor current $I_{(IDE)}$ (31), wherein a shunt current $I_{(N)}$ (36, 37) is determined for a triggering threshold (38) for the sensor current $I_{(IDE)}$ (31) at which a regeneration of the particle sensor (10) is started, and a corrected triggering threshold (39) is determined with said shunt current $I_{(N)}$ (36, 37) as an offset correction.

2. The method according to claim 1, wherein the sensor current $I_{(IDE)}$ (31) is determined when a minimum value (35) of the sensor current $I_{(IDE)}$ (31) is reached.

3. The method according to claim 1, wherein the sensor current $I_{(IDE)}$ (31) is determined after a certain waiting time (34) after a certain sensor element temperature threshold has been undershot.

4. The method according to claim 1, wherein the sensor current $I_{(IDE)}$ (31) is determined directly when the sensor element temperature threshold is undershot.

5. A method according to claim 1, characterized in that the shunt diagnosis is carried out after a sensor regeneration.

6. A method according to claim 1, characterized in that the shunt diagnosis is carried out after a certain time after the switching off of the heating element (14), wherein the time is predefined by means of a timer.

7. The method according to claim 1, characterized in that, the regeneration of the particle sensor (10) is started with a time delay when the triggering threshold (38) is reached, as a function of the shunt current $I_{(N)}$ (36, 37).

8. A method according to claim 1, characterized in that the offset correction of the triggering threshold (38) is carried out after a sensor regeneration.

9. A method according to claim 1, characterized in that the offset correction of the triggering threshold (38) is carried out after a certain time after the switching off of the heating element (14), wherein the time is predefined by means of a timer.

10. A method according to claim 1, characterized in that the shunt current $I_{(N)}$ (36, 37) which is determined during the shunt diagnosis is subtracted from the measured sensor current $I_{(IDE)}$ (31) during the normal operation.

11. A method according to claim 1, characterized in that the shunt current $I_{(N)}$ (36, 37) which is determined during the shunt diagnosis is compared with a fixed, predefined threshold value.

12. A method according to claim 1, characterized in that the shunt current $I_{(N)}$ (36, 37) which is determined during the shunt diagnosis is compared with a temperature-dependent threshold value for a maximum shunt current $I_{(N)}$.

13. A method according to claim 1, characterized in that the shunt current $I_{(N)}$ (36, 37) which is determined during the shunt diagnosis is determined multiple times and averaged.

14. A method according to claim 1, characterized in that the shunt current $I_{(N)}$ (36, 37) which is determined during the shunt diagnosis is determined by means of a low-pass filter.

15. A method according to claim 1, characterized in that a resistance or a conductance value between the electrodes (12, 13) of the sensor structure is evaluated as an equivalent variable for the sensor current $I_{(IDE)}$ (31).

16. Use of the method according to claim 1 within the scope of an on-board diagnosis in a diesel internal combustion engine.

17. A device for operating a particle sensor (10), wherein the particle sensor (10) has at least two inter-digital electrodes (12, 13) which engage one in the other and to which a sensor voltage $U_{(IDE)}$ (21) can be applied in order to determine loading of the particle sensor (10) with soot particles (16), and a sensor current $I_{(IDE)}$ (31) across the electrodes (12, 13) can be measured and evaluated, wherein the particle sensor (10) is connected to a controller having devices for diagnosing the loading of the particle sensor (10) with soot, characterized in that the controller has devices for determining a shunt current $I_{(N)}$ (36, 37), and, on the basis of the shunt current $I_{(N)}$ (36, 37), corrects a triggering threshold (38) for regeneration of the particle sensor (10) or to perform self-diagnosis of the particle sensor (10).

18. The device according to claim 17, wherein the controller is an engine controller.

19. The device according to claim 17, wherein the controller is a sensor control unit.

* * * * *